US00PP37252P2

(12) United States Plant Patent
von Tubeuf

(10) Patent No.: US PP37,252 P2
(45) Date of Patent: Feb. 10, 2026

(54) ***BIDENS* PLANT NAMED 'KLEBF24674'**

(50) Latin Name: *Bidens ferulifolia*
Varietal Denomination: KLEBF24674

(71) Applicant: KLEMM + SOHN GMBH & CO. KG, Stuttgart (DE)

(72) Inventor: Guido von Tubeuf, Stuttgart (DE)

(73) Assignee: KLEMM + SOHN GMBH & CO. KG, Stuttgart (DE)

( * ) Notice: Subject to any disclaimer, the term of this patent is extended or adjusted under 35 U.S.C. 154(b) by 0 days.

(21) Appl. No.: 19/278,321

(22) Filed: Jul. 23, 2025

(51) Int. Cl.
*A01H 5/02* (2018.01)
*A01H 6/14* (2018.01)

(52) U.S. Cl.
USPC ..... Plt./409

(58) Field of Classification Search
USPC ..... Plt./263.1, 409
See application file for complete search history.

(56) References Cited

U.S. PATENT DOCUMENTS

PP30,467 P2 * 4/2019 Koot ..... A01H 5/02
Plt./410

* cited by examiner

*Primary Examiner* — Karen M Redden
(74) *Attorney, Agent, or Firm* — Weatherly IP Solutions, LLC; John E. Pritchard; James M. Weatherly

(57) ABSTRACT

A new *Bidens* plant particularly distinguished by red flowers with yellow centers; and an upright to semi-trailing habit, is disclosed.

1 Drawing Sheet

Genus and species: *Bidens ferulifolia.*
Variety denomination: 'KLEBF24674'.

BACKGROUND OF THE NEW PLANT

The present invention comprises a new and distinct variety of *Bidens*, botanically known as *Bidens ferulifolia* and hereinafter referred to by the variety name 'KLEBF24674'. 'KLEBF24674' originated from a controlled-cross between female parent 'KLEBF21466' (unpatented) and an unknown male parent.

In July 2020, the female parent KLEBF21466 was crossed with an unknown *Bidens* male in Stuttgart, Germany and seeds were obtained. The seeds were sown and plants were grown for evaluation. A plant line was selected in May 2021 and subsequently named 'KLEBF24674'. In May 2021 'KLEBF24674' was first vegetatively propagated by apical cuttings in Stuttgart, Germany. 'KLEBF24674' was found to reproduce true to type in successive generations of asexual propagation via vegetative cuttings in Stuttgart, Germany.

SUMMARY

The following are the most outstanding and distinguishing characteristics of this new variety when grown under normal horticultural practices in Stuttgart, Germany.

1. Red flowers with yellow centers; and
2. An upright to semi-trailing habit.

DESCRIPTION OF THE PHOTOGRAPH

This new *Bidens* plant is illustrated by the accompanying photograph which shows an overall view of the plant. The photograph is of an approximately 13-week-old plant grown outdoors in Stuttgart, Germany in August 2024. The colors shown are as true as can be reasonably obtained by conventional photographic procedures.

DESCRIPTION OF THE NEW VARIETY

The following detailed descriptions set forth the distinctive characteristics of 'KLEBF24674'. The data which define these characteristics were collected from asexual reproductions carried out in Stuttgart, Germany. In May 2025, data was collected on plants that had been growing for 8 weeks after potting in a greenhouse in Stuttgart, Germany. Color references are to The R.H.S. Color Chart of The Royal Horticultural Society of London (R.H.S.), 5$^{th}$ edition (2007).

Classification:
- *Family.*—Asteraceae.
- *Botanical.*—*Bidens ferulifolia.*
- *Common.*—*Bidens.*
- *Designation.*—'KLEBF24674'.

Parentage:
- *Female parent.*—KLEBF21466 (unpatented).
- *Male parent.*—Unknown.

Plant:
- *Habit.*—Upright to semi-trailing.
- *Height.*—21.0 cm.
- *Spread.*—17.0 cm.
- *Life cycle.*—Annual.
- *Time to produce a rooted cutting.*—3 weeks.
- *Root description.*—White, fine.
- *Rooting habit.*—Freely branching.
- *Time to bloom from propagation.*—6 to 7 weeks from potting date.
- *Branching habit.*—Freely branching.

Lateral branches:
- *Quantity per plant.*—25 to 30.
- *Strength.*—Fine to Medium.
- *Color.*—RHS 143C.

*Pubescence*.—Present.
*Diameter*.—0.15 cm.
*Length*.—5.0 cm to 6.0 cm.
*Internode length*.—1.5 cm to 3.0 cm.
*Anthocyanin*.—Weak.

Foliage:
*Arrangement*.—Opposite.
*Length*.—2.0 cm to 3.0 cm.
*Width*.—2.5 cm to 3.0 cm.
*Shape*.—Pinnate (3 single leaflets composed to one leaf).
*Apex*.—Acute.
*Base*.—Attenuate (leaflets).
*Margin*.—Lobed to serrate (leaflets).
*Texture*.—Upper surface: Smooth. Lower surface: Smooth.
*Venation pattern*.—Pinnate.
*Color of developing leaves* (*immature*).—Upper surface: RHS 137A, towards middle vein RHS 137B. Lower surface: RHS 137B (margin), 138B (center). Venation color: Upper surface: RHS 138B. Lower surface: RHS 138B. Color of fully expanded leaves (mature): Upper surface: RHS 137A, towards middle vein RHS 137B. Lower surface: RHS 137B (margin), RHS 138B (center). Venation color: Upper surface: RHS 138B. Lower surface: RHS 138B.
*Petiole*.—Length: 0.5 cm to 1.0 cm. Diameter: 0.1 cm. Color: Green overlaid with anthocyanin (no RHS available). Texture: Slightly pubescent.

Inflorescence:
*Appearance*.—Composite (ray and disc florets).
*Flowering habit*.—Continuous.
*Lastingness of inflorescence on the plant*.—7 to 8 days.
*Number of inflorescences and buds per plant*.—About 25 inflorescences open at the same time plus about 10 flower buds.
*Fragrance*.—Present.
*Natural flowering season*.—April to November.
*Diameter*.—About 3.5 cm.
*Depth*.—0.5 cm.
*Disc diameter*.—0.7 cm to 0.9 cm.

Flower buds:
*Length*.—0.5 cm.
*Diameter*.—0.4 cm.
*Surface texture*.—Smooth.
*Shape*.—Ovate.
*Color*.—RHS 191B.

Ray florets:
*Quantity per inflorescence*.—6 to 8.
*Length*.—1.3 cm to 1.5 cm.
*Width*.—1.0 cm to 1.1 cm.
*Shape*.—Ovate.
*Apex*.—Obtuse, but showing 1 sharp tip on top in the middle plus 2 broader tips left and right (depth less than 0.05 cm).
*Base*.—Fused bottom 0.1 cm.
*Margin*.—Entire.
*Color, when opening*.—Upper surface: RHS 45A. Lower surface: RHS45A with yellow stripes.
*Color, when fully open*.—Upper surface: RHS 45A to 34A (in parallel when all disc florets are open). Lower surface: RHS 34A.
*Surface texture*.—Upper surface: Smooth. Lower surface: Smooth.

Disc florets:
*Quantity per inflorescence*.—*About* 50.
*Length*.—0.4 cm to 0.5 cm.
*Width*.—0.05 cm.
*Shape*.—Tubular.
*Apex*.—Five-pointed.
*Base*.—Fused.
*Margin*.—Entire.
*Color, when opening*.—Upper surface: RHS 9C. Lower surface: RHS 9C.
*Color, when fully open*.—Upper surface: RHS 9B. Lower surface: RHS 9B.
*Surface texture*.—Upper surface: Smooth. Lower surface: Smooth.

Phyllaries:
*Quantity per inflorescence*.—*About* 14.
*Length*.—0.5 to 0.6 cm.
*Width*.—0.1 cm.
*Shape*.—Between spatulate and cuneate.
*Apex*.—Mucronate.
*Base*.—Fused.
*Margin*.—Entire.
*Surface texture*.—Upper surface: Smooth. Lower surface: Smooth.
*Color*.—Upper surface: RHS N137A to RHS 137C, with some having RHS 177A with yellowish/greyish margin. Lower surface: RHS N137A to 137C.

Peduncle:
*Length*.—About 3 cm.
*Diameter*.—0.1 cm.
*Color*.—RHS 143A.
*Texture*.—Slightly pubescent.
*Strength*.—Weak to medium.

Reproductive organs:
*Androecium*.—Present on disc florets only. Quantity of stamens per floret: 5. Filament length: 0.4 cm. Filament color: RHS 200A. Anther length: 0.1 cm to 0.15 cm. Anther color: RHS 200A. Pollen amount: Abundant. Pollen color: RHS between 17A and 21A.
*Gynoecium*.—Present on ray florets only. Quantity of pistils per floret: 1. Pistil length: 0.3 cm. Style length: 0.2 cm. Style color: RHS 15A. Stigma shape: Two parted. Stigma color: RHS 15A. Ovary color: RHS 149C.

Fruit and seed set: None observed.
Disease and pest/insect resistance: None observed.

COMPARISON WITH PARENTAL LINES AND KNOWN VARIETY

'KLEBF24674' is distinguished from its parents as described in Table 1:

TABLE 1

Comparison with Parental Lines

| Trait | 'KLEBF24674' | Female parent 'KLEBF21466' |
|---|---|---|
| Color pattern | Red flowers with a yellow center | Yellow flamed red |

'KLEBF24674' can be compared to the commercial variety 'Bidy Boom Red' (patent status unknown). Differences between the two varieties are described in Table 2:

TABLE 2

| Comparison with Similar Variety | | |
|---|---|---|
| Trait | 'KLEBF24674' | Commercial line Bidy Boom Red |
| Flower color | Red flowers with a yellow flower color. The red is a darker shade of red than Bidy Boom Red and the yellow is more distinct that Bidy Boom Red | Flower color has a lighter shade of red than 'KLEBF24674' and the yellow center is less distinct than 'KLEBF24674' |

TABLE 2-continued

| Comparison with Similar Variety | | |
|---|---|---|
| Trait | 'KLEBF24674' | Commercial line Bidy Boom Red |
| Earliness | Earlier than Bidy Boom Red | Later than 'KLEBF24674' |

I claim:

1. A new and distinct variety of *Bidens* plant named 'KLEBF24674' as illustrated and described herein.

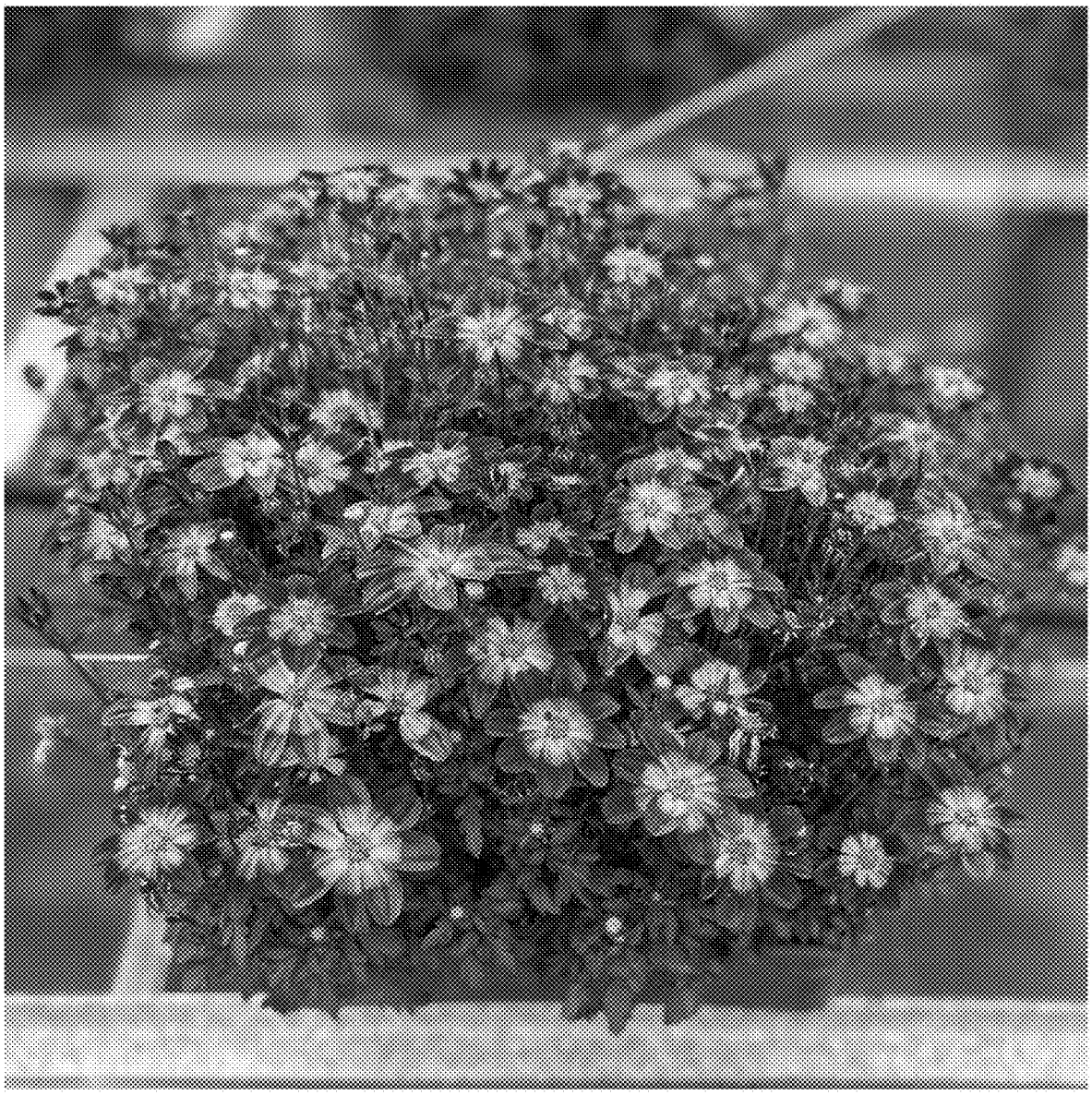

* * * * *